United States Patent
Rodrigues, Jr. et al.

(10) Patent No.: US 9,289,234 B2
(45) Date of Patent: Mar. 22, 2016

(54) ACCESS DEVICE INCLUDING SHAPE MEMORY DEPLOYMENT MECHANISM

(71) Applicant: Covidien LP, Mansfield, MA (US)

(72) Inventors: Anibal Rodrigues, Jr., Milford, CT (US); Greg Okoniewski, North Haven, CT (US)

(73) Assignee: Covidien LP, Mansfield, MA (US)

( * ) Notice: Subject to any disclaimer, the term of this patent is extended or adjusted under 35 U.S.C. 154(b) by 17 days.

(21) Appl. No.: 14/172,049

(22) Filed: Feb. 4, 2014

(65) Prior Publication Data

US 2014/0155699 A1    Jun. 5, 2014

Related U.S. Application Data

(63) Continuation of application No. 13/224,355, filed on Sep. 2, 2011, now Pat. No. 8,679,151.

(60) Provisional application No. 61/416,764, filed on Nov. 24, 2010.

(51) Int. Cl.
  *A61B 17/02* (2006.01)
  *A61B 17/34* (2006.01)
  (Continued)

(52) U.S. Cl.
  CPC ......... *A61B 17/3423* (2013.01); *A61B 17/0218* (2013.01); *A61B 2017/00867* (2013.01); *A61B 2017/047* (2013.01); *A61B 2017/0409* (2013.01); *A61B 2017/0412* (2013.01); *A61B 2017/0472* (2013.01); *A61B 2017/3445* (2013.01); *A61B 2017/3488* (2013.01)

(58) Field of Classification Search
  CPC ........... A61B 17/02; A61B 2017/0212; A61B 17/0218; A61B 2017/0225
  See application file for complete search history.

(56) References Cited

U.S. PATENT DOCUMENTS 5,176,128 A * 1/1993 Andrese .................. 600/204
5,257,975 A   11/1993 Foshee
5,279,564 A   1/1994 Taylor (Continued)

FOREIGN PATENT DOCUMENTS

EP    2005907       12/2008
EP    2005907 A2    12/2008

(Continued)

OTHER PUBLICATIONS

European Search Report for corresponding EP 11 25 0793 mailed Jun. 5, 2012; (10 pages).

(Continued)

*Primary Examiner* — Jerry Cumberledge

(57) ABSTRACT

A surgical access device is disclosed which includes a housing, a collar, and a plurality of deformable members. The housing defines a proximal end and a distal end and has a plurality of lumens extending therethrough. The collar is repositionable between a first position and a second position with the second position being closer to the proximal end of the housing than the first position. Each of the plurality of deformable members defines a distal portion, is coupled to the collar and is transitionable through one of the plurality of lumens. The plurality of deformable members is in a retracted state when the collar is in the first position and a deployed state when the collar is in the second position. One or more of the plurality of deformable members may also include a barb attached to the distal portion.

19 Claims, 4 Drawing Sheets

(51) Int. Cl.
*A61B 17/00* (2006.01)
*A61B 17/04* (2006.01)

(56) References Cited

U.S. PATENT DOCUMENTS

| | | | |
|---|---|---|---|
| 5,290,249 | A | 3/1994 | Foster et al. |
| 5,354,271 | A | 10/1994 | Voda |
| 5,540,648 | A | 7/1996 | Yoon |
| 5,887,594 | A | 3/1999 | LoCicero, III |
| 6,033,426 | A | 3/2000 | Kaji |
| 6,048,309 | A | 4/2000 | Flom et al. |
| 6,461,366 | B1 * | 10/2002 | Seguin .................. 606/144 |
| 6,488,692 | B1 | 12/2002 | Spence et al. |
| 7,217,277 | B2 | 5/2007 | Parihar et al. |
| 7,731,655 | B2 * | 6/2010 | Smith et al. .................. 600/217 |
| 8,192,419 | B2 | 6/2012 | Li et al. |
| 8,409,090 | B2 | 4/2013 | Smith et al. |
| 8,679,151 | B2 * | 3/2014 | Rodrigues et al. ............ 606/206 |
| 2004/0092795 | A1 | 5/2004 | Bonadio et al. |
| 2004/0225194 | A1 | 11/2004 | Smith et al. |
| 2008/0319261 | A1 | 12/2008 | Lucini |
| 2009/0137878 | A1 * | 5/2009 | Rivera et al. .................. 600/206 |
| 2009/0326332 | A1 | 12/2009 | Carter |
| 2010/0179588 | A1 | 7/2010 | Sater et al. |
| 2010/0249517 | A1 | 9/2010 | Fischvogt et al. |
| 2010/0249523 | A1 | 9/2010 | Spiegal et al. |
| 2010/0312064 | A1 | 12/2010 | Weisenburgh et al. |
| 2011/0040154 | A1 * | 2/2011 | Reznik .......................... 600/227 |
| 2011/0071362 | A1 * | 3/2011 | Reicher .............. A61B 17/0218 600/217 |
| 2011/0087067 | A1 * | 4/2011 | Rodrigues et al. .............. 600/37 |
| 2011/0087249 | A1 * | 4/2011 | Rodrigues et al. .............. 606/151 |
| 2011/0125186 | A1 * | 5/2011 | Fowler ............... A61B 17/3423 606/213 |
| 2011/0224742 | A1 * | 9/2011 | Weisel ............... A61B 17/0218 606/86 R |
| 2016/0000461 | A1 * | 1/2016 | Litvack ............. A61B 17/3423 600/204 |

FOREIGN PATENT DOCUMENTS

| | | |
|---|---|---|
| EP | 2238925 | 10/2010 |
| JP | 2009-028666 | 2/1997 |
| JP | 2006-501023 | 1/2006 |
| JP | 2010-005391 | 1/2010 |
| WO | WO 2004/030515 | 4/2004 |
| WO | WO 2004/075741 | 9/2004 |
| WO | WO 2009/048542 | 4/2009 |

OTHER PUBLICATIONS

European Office Action dated Mar. 20, 2015, issued in European Appln. No. 11250793.

JP Office Action corresponding to JP 2011-199484 dated Apr. 6, 2015; and English Translation; 6 pp.

* cited by examiner

ACCESS DEVICE INCLUDING SHAPE MEMORY DEPLOYMENT MECHANISM

CROSS REFERENCE TO RELATED APPLICATION

This application is a continuation of U.S. patent application Ser. No. 13/224,355 filed Sep. 2, 2011, now U.S. Pat. No. 8,679,151, which claims benefit of U.S. Provisional Application No. 61/416,764 filed on Nov. 24, 2010, and the disclosures of each of the above-identified applications are hereby incorporated by reference in their entirety.

BACKGROUND

1. Technical Field

The present disclosure relates generally to a port assembly for use in minimally invasive surgical procedures, such as endoscopic or laparoscopic type procedures, and more particularly to a device and a method for releasably securing an access device in tissue.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", unless performed on the patient's abdomen, in which case the procedure is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses (e.g. $CO_2$) are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various ports with valves and seals are used during the course of minimally invasive procedures and are widely known in the art. However, a continuing need exists for a surgical portal apparatus that can be easily and releasably secured in an incision in tissue to facilitate the accessibility of an underlying tissue site with relative ease and with minor inconvenience for the surgeon.

SUMMARY

Disclosed herein are devices for deploying and securing an access seal within a body cavity and a method for using those devices.

A surgical access device is disclosed which includes a housing, a collar, and a plurality of deformable members. The housing defines a proximal end and a distal end and has a plurality of lumens extending therethrough. The plurality of lumens may be adapted for sealed reception of surgical objects. The collar is repositionable between a first position and a second position with the second position being closer to the proximal end of the housing than the first position. Each deformable member is coupled to the collar and defines a distal portion. Each deformable member is transitionable through one of the plurality of lumens. The plurality of deformable members is in a retracted state when the collar is in the first position and a deployed state when the collar is in the second position.

In one embodiment, the distal portions of the plurality of deformable members are curled toward an inner surface of tissue when in the deployed state and may be in contact with or embed into the inner surface of tissue. The distal portions of the plurality of deformable members may be essentially linear when in the retracted state and may be biased towards the deployed state. The plurality of deformable members may be made from a shaped memory material such as, for example, nitinol, and may be formed as wires.

In another embodiment, one or more of the plurality of deformable members includes a barb attached to the distal portion thereof. The barb may also be releasably attached and may be made of a bio-absorbable material. One or more of the deformable members may also include a suture attached to the barb and may define passageways therethrough for the reception of the suture.

A method of securing a surgical access device in an incision in tissue is disclosed. The method includes providing a surgical access device including a housing, a collar and a plurality of deformable members. The housing defines a proximal end and a distal end and has a plurality of lumens extending therethrough. The collar is repositionable between a first position and a second position, the second position being closer to the proximal end of the housing than the first position. The plurality of deformable members defines distal portions and each deformable member is coupled to the collar and transitionable through one of the plurality of lumens. The plurality of deformable members are in a retracted state when the collar is in the first position and a deployed state when the collar is in the second position.

The method includes the steps of inserting the surgical access device into an incision in tissue, actuating the collar from the first position to the second position and actuating the collar from the second position to the first position. During actuation from the first position to the second position, the plurality of deformable members is transitioned between the retracted state and the deployed state. During actuation from the second position to the first position the plurality of deformable members are transitioned between the deployed state and the retracted state. One or more of the plurality of deformable members may also include a barb releasably attached to the distal portion thereof. A suture may be attached to the barb and one or more of the plurality of deformable members may define a passageway therethrough for reception of the suture. The barb at least partially embeds into an inner surface of tissue when the plurality of deformable members transition from the retracted state to the deployed state and remains at least partially embedded into an inner surface of tissue when the plurality of deformable members transition from the deployed state to the retracted state. The method may also include the step of removing the surgical access device from the incision in tissue. During removal the barbs remain at least partially embedded into an inner surface of tissue and the sutures play out from the passageways of one or more of the deformable members to enable the surgeon to tie off the incision.

The various aspects of this disclosure will be more readily understood from the following detailed description when read in conjunction with the appended drawings.

BRIEF DESCRIPTION OF THE DRAWINGS

Embodiments of the disclosure will be described with reference to the accompanying drawings in which.

DETAILED DESCRIPTION

Figure 2:
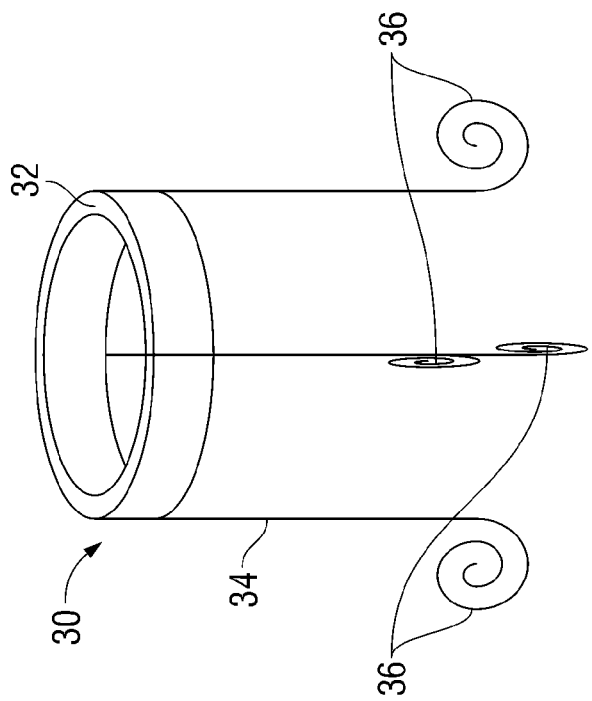
FIG. 2 is a perspective view of the collar of the surgical access device of FIG. 1.

Particular embodiments of the present disclosure will be described herein with reference to the accompanying drawings, wherein like reference numerals identify similar or identical elements. As shown in the drawings and as described throughout the following description, and as is traditional when referring to relative positioning on an object, the term proximal refers to the end of the device that is closer to the user and the term distal refers to the end of the apparatus that is further from the user. Devices are discussed in terms for use through an incision, but it is contemplated that they can be used through any naturally occurring orifice (mouth, anus, vagina, etc.). In the following description, well-known functions or constructions are not described in detail to avoid obscuring the present disclosure in unnecessary detail.

Figure 1:
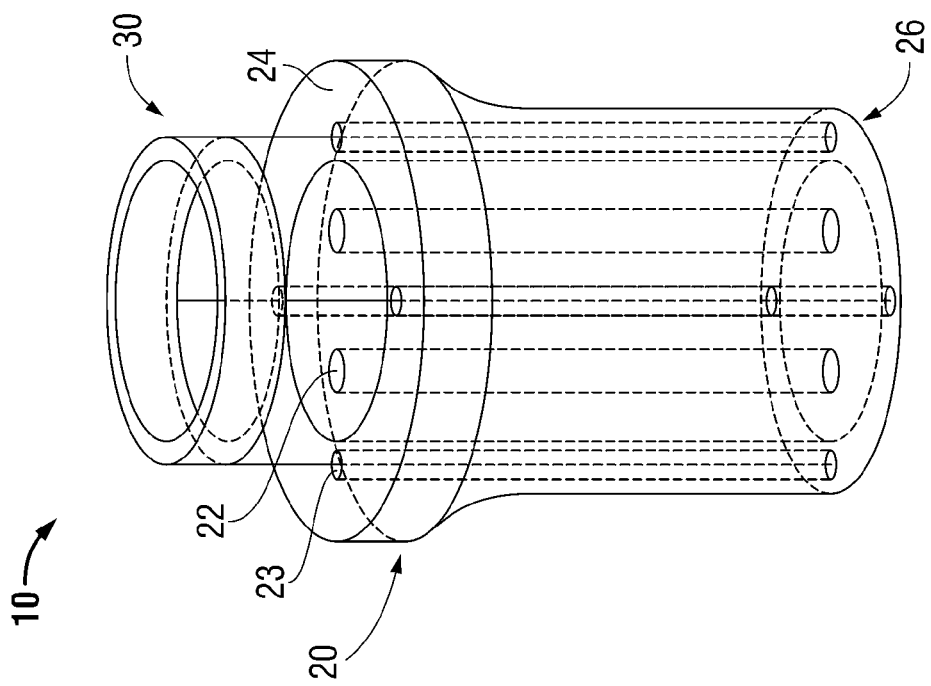
FIG. 1 is a perspective view of a surgical access device according to an embodiment of this disclosure.

Referring now to FIG. 1, there is disclosed a surgical access device 10 including a housing 20 and an anchor 30. Housing 20, defining a proximal end 24 and a distal end 26, includes a plurality of surgical lumens 22 and a plurality of anchor lumens 23 extending longitudinally therethrough. Housing 20 is adapted for sealed insertion into an incision in tissue and surgical lumens 22 may be adapted to receive surgical objects therethrough in a substantially sealed manner for performing a surgical operation. Surgical lumens 22 and anchor lumens 23 may include sealing valves for inhibiting the loss of insufflation fluids therethrough such as, for example, duck-bill valves, flapper valves, or other valves as known in the art.

Referring now to FIG. 2, anchor 30 includes a collar 32 and a plurality of deformable members 34 coupled to collar 32 and extending distally therefrom. Distal portions 36 of deformable members 34 are biased in a curled or curved state, as shown. Deformable members 34 are adapted for insertion through anchor lumens 23. Anchor lumens 23 may be adapted to receive deformable members 34 in a substantially sealed manner.

Figure 3:
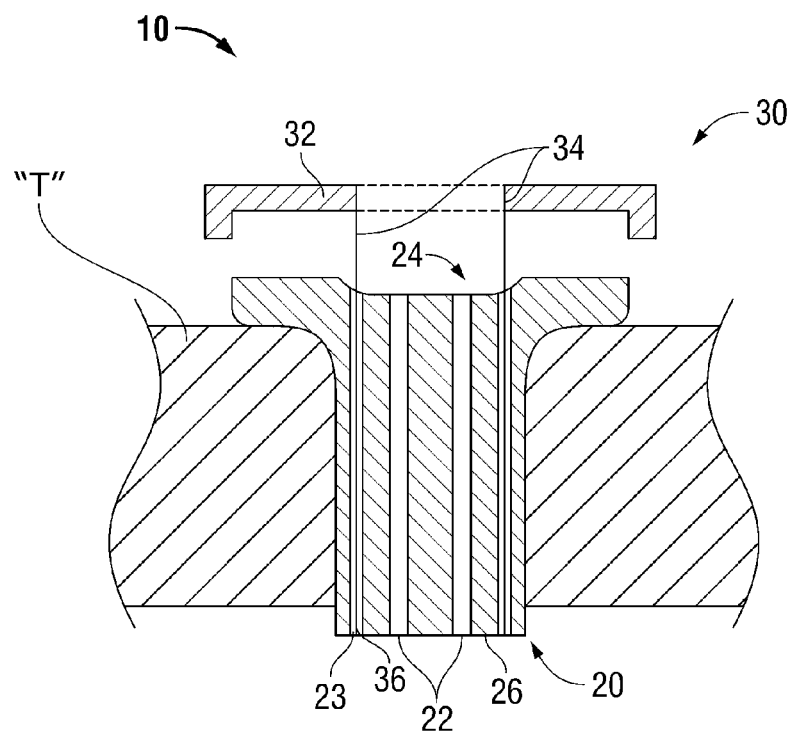
FIG. 3 is side cross-sectional view of the surgical access device of FIG. 1 when inserted in tissue.
Figure 4:
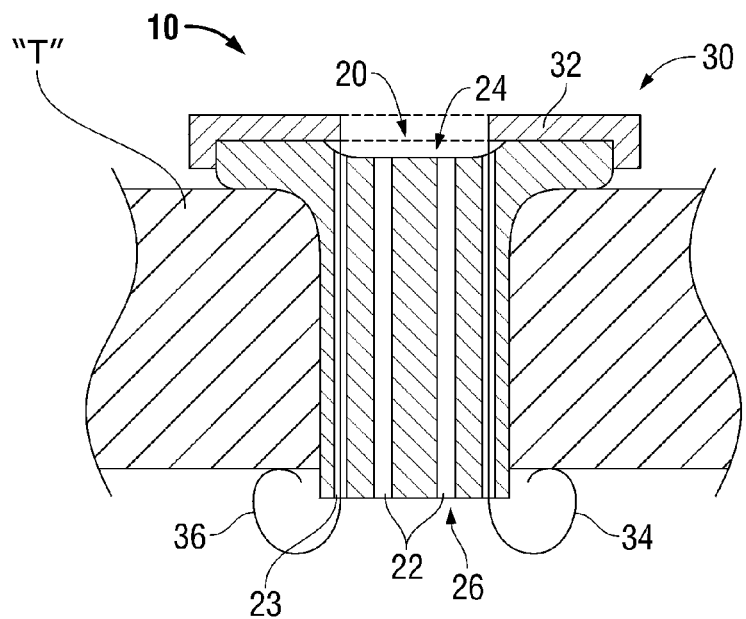
FIG. 4 is side cross-sectional view of the surgical access device of FIG. 1 when inserted in tissue with the collar deployed.

Referring now to FIGS. 3 and 4, anchor 30 is repositionable between a first position (FIG. 3) and a second position (FIG. 4). In the first position collar 32 is spaced apart from proximal end 24 of housing 20 and distal portions 36 of deformable members 34 are retracted within anchor lumens 23. The distal portions 36 of deformable members 34 are normally biased towards a curled or curved state (FIGS. 2 and 4) and while retracted, distal portions 36 of deformable members 34 are restrained in an essentially linear state (FIGS. 1 and 3). Some part of distal portions 36 of deformable members 34 may alternatively protrude from anchor lumens 23 when anchor 30 is in the first position. In the second position, collar 32 is closer to proximal end 24 of housing 20 and deformable members 34 extend past distal end 26 of housing 20. Distal portions 36 of deformable members 34 are released from anchor lumens 23 and allowed to curl or curve toward an inner wall of tissue "T". Distal portions 36 of deformable members 34 may also contact an inner wall of tissue "T" or may become embedded in an inner wall of tissue "T". Deformable members 34 may be made from a shape memory material such as, for example, nitinol or shape memory polymers. Deformable members 34 may also be formed as a wire.

During use, housing 20 is inserted into an incision in tissue "T" and collar 32 is actuated to transition anchor 30 from the first position (FIG. 3) to the section position (FIG. 4). During actuation of collar 32, deformable members 34 move distally through anchor lumens 23. Distal portions 36 of deformable members 34 exit anchor lumens 23 and, no longer being restrained by anchor lumens 23, curl or curve toward an inner wall of tissue "T" to secure housing 20 in place for use during a surgical operation. Once the surgical operation is complete collar 32 is actuated to transition anchor 30 from the second position (FIG. 4) to the first position (FIG. 3). Distal portions 36 of deformable members 34 are uncurled as they retract proximally into anchor lumens 23 and become restrained in an essentially linear state. Housing 20, now unsecured, may be removed from the incision.

Figure 5:
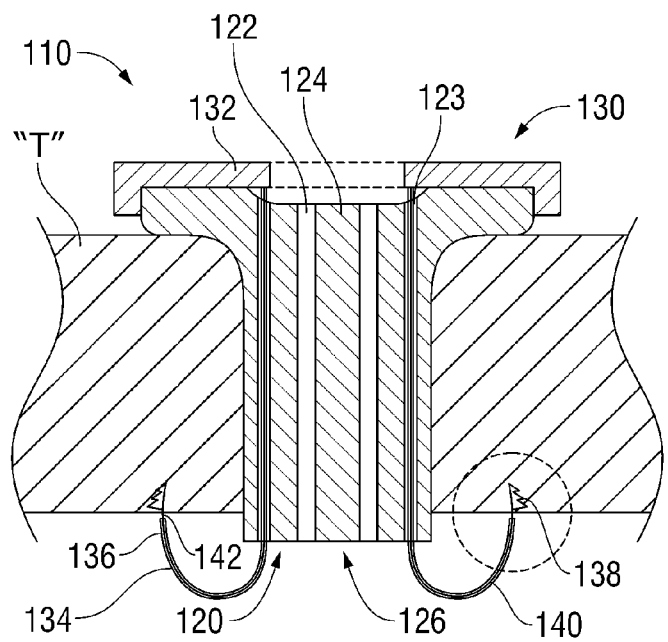
FIG. 5 is a cross-sectional view of a surgical access device according to an alternate embodiment of this disclosure.
Figure 5A:
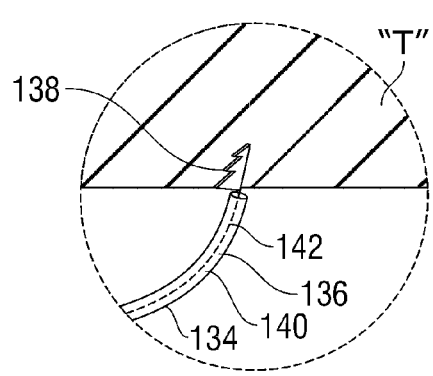
FIG. 5a an enlarged view of the deformable member of surgical access device of FIG. 5 when in the deployed state with the barb embedded into tissue.
Figure 5B:
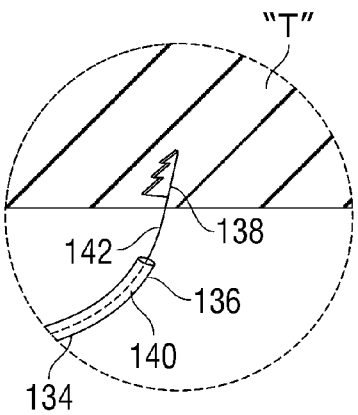
FIG. 5b an enlarged view of the deformable member of surgical access device of FIG. 5 with the barb detached and embedded into tissue.

Referring now to FIGS. 5, 5A and 5B, another embodiment of a surgical access device 110 in accordance with the present disclosure, is illustrated. In the interest of brevity, the present embodiment will focus on the differences between the previously described surgical access device 10 and surgical access device 110. Surgical access device 110 includes an anchor 130 having a collar 132 and a plurality of deformable members 134, as described above. In this embodiment, one or more of deformable members 134 may include a barb or barbs 138 attached to distal portions 136. Barbs 138 may also be releasably attached to deformable members 134. Barbs 138 may be detached from deformable members 134 after at least partially embedding into an inner surface of tissue and may be bio-absorbable. Deformable members 134 may also define passageways 140 for the reception of sutures 142 therethrough. Sutures 142 are attached to barbs 138 such that when barbs 138 detach from deformable members 134, sutures 142 remain attached to barbs 138. It is contemplated that, when sutures are used, at least two deformable members 134 have barbs 138 with attached sutures 142 to facilitate tying off and closing of the incision. The full length of sutures 142 may be stored within passageways 140 to be played out as surgical access device 110 is removed from the incision or the sutures may extend through passageways 140 and out of proximal openings (not shown) in passageways 140.

Figure 6:
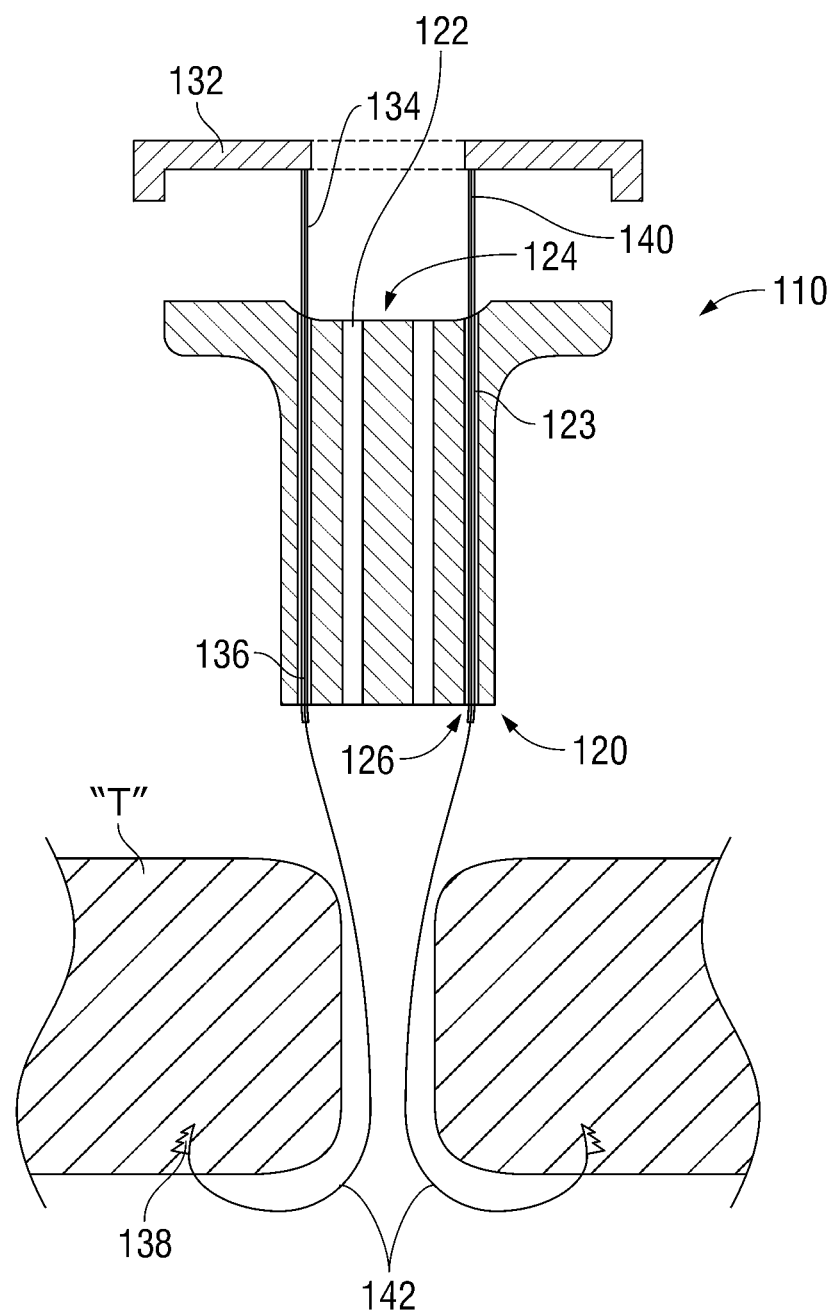
FIG. 6 is a cross-sectional view of the surgical access device of FIG. 5 with the surgical access device removed from the incision in tissue.

During use as described above and seen in FIGS. 5, 5A, 5B and 6, when collar 132 is actuated from the first position to the second position distal portions 136 of deformable members 134 exit anchor lumens 123 and, no longer being restrained by anchor lumens 123, curl or curve toward an inner wall of tissue "T". When distal portions 136 of deformable members 134 come into contact with inner wall of tissue "T", barbs 138 are at least partially embedded into inner wall of tissue "T" as seen in FIGS. 5 and 5A. When collar 132 is then actuated from the second position to the first position and distal portions 136 of deformable members 134 are uncurled as they retract proximally into anchor lumens 123, barbs 138 are detached and remain embedded into the inner wall of tissue "T" as seen in FIG. 5B. Sutures 142 remain attached to barbs 138 and extend out of passageways 140. When surgical access device 110 is removed from the incision, sutures 142 are allowed to play out of passageways 140 to provide the surgeon with a sufficient length of suture to close the incision (FIG. 6). Sutures 140 may then be detached from passageways 140 and tied off by the surgeon.

It will be understood that various modifications may be made to the embodiments disclosed herein. Therefore, the above description should not be construed as limiting, but merely as exemplifications of particular embodiments. Those skilled in the art will envision other modifications within the scope and spirit of the claims appended hereto.

The invention claimed is:

1. A surgical access device comprising:
a housing defining a proximal end and a distal end, the housing having at least two surgical lumens and a plurality of anchor lumens extending therethrough;
an anchor having a collar defining an opening, the collar being movable with respect to the housing from a first position to a second position, the second position being closer to the proximal end of the housing than the first position; and
a plurality of deformable members, each deformable member extending distally from the collar and being movable through one of the plurality of anchor lumens, the plurality of deformable members being movable with respect to the housing in response to movement of the collar from the first position to the second position, wherein one or more of the plurality of deformable members includes a bio-absorbable barb attached to a distal portion thereof.

2. The surgical access device of claim 1, wherein the plurality of deformable members is movable toward a deployed position when the collar is moved toward its second position, and wherein distal portions of the plurality of deformable members are curled toward an inner surface of tissue when in the deployed position.

3. The surgical access device of claim 2, wherein the distal portions of the plurality of deformable members contact the inner surface of tissue when in the deployed position.

4. The surgical access device of claim 2, wherein the distal portions of the plurality of deformable members are configured to become imbedded into the inner surface of tissue when in the deployed position.

5. The surgical access device of claim 2, wherein the distal portions of the plurality of deformable members are biased toward the deployed position.

6. The surgical access device of claim 1, wherein the plurality of deformable members is in a retracted position when the collar is in its first position, and wherein the distal portions of the plurality of deformable members are linear when in the retracted position.

7. The surgical access device of claim 1, wherein the plurality of deformable members is wires.

8. The surgical access device of claim 1, wherein the plurality of deformable members is made from a shape memory material.

9. The surgical access device of claim 8, wherein the shape memory material is nitinol.

10. The surgical access device of claim 1, wherein one or more of the at least one surgical lumens is adapted for sealed reception of a surgical object.

11. The surgical access device of claim 1, wherein the bio-absorbable barb attached to the distal portion of one or more of the plurality of deformable members is releasably attached thereto.

12. The surgical access device of claim 1, wherein one or more of the plurality of deformable members includes a suture attached to the barb.

13. The surgical access device of claim 12, wherein one or more of the plurality of deformable members defines a passageway therethrough for the reception of the suture.

14. The surgical access device of claim 1, wherein the collar is repositionable between the first position and the second position.

15. The surgical access device of claim 1, wherein the plurality of deformable members is in a retracted position when the collar is in the first position, and wherein the plurality of deformable members is in a deployed position when the collar is in the second position.

16. The surgical access device of claim 1, wherein a diameter of the opening is greater than a diameter of each surgical lumen of the at least two surgical lumens.

17. A surgical access device comprising:
a housing defining a proximal end and a distal end, the housing having at least one surgical lumen and a plurality of anchor lumens extending therethrough;
an anchor having a collar defining an opening, the collar being movable with respect to the housing from a first position to a second position, the second position being closer to the proximal end of the housing than the first position; and
a plurality of deformable members, each deformable member extending distally from the collar and being movable through one of the plurality of anchor lumens, the plurality of deformable members being movable with respect to the housing in response to movement of the collar from the first position to the second position, wherein a diameter of the opening is greater than a diameter of each of the at least one surgical lumen, and wherein one or more of the plurality of deformable members includes a bio-absorbable barb attached to a distal portion thereof.

18. A surgical access device comprising:
a housing defining a proximal end and a distal end, the housing having at least one surgical lumen and a plurality of anchor lumens extending therethrough;
an anchor having a collar defining an opening, the collar being movable with respect to the housing from a first position to a second position, the second position, the second position being closer to the proximal end of the housing than the first position; and
a plurality of deformable members, each deformable member extending distally from the collar and being movable through one of the plurality of anchor lumens, the plurality of deformable members being movable with respect to the housing in response to movement of the collar from the first position to the second position, wherein a diameter of the opening is greater than a diameter of each of the at least one surgical lumen, wherein one or more of the plurality of deformable members includes a barb attached to a distal portion thereof, and wherein one or more of the plurality of deformable members includes a suture attached to the barb.

19. A surgical access device comprising:
a housing defining a proximal end and a distal end, the housing having at least two surgical lumens and a plurality of anchor lumens extending therethrough;
an anchor having a collar defining an opening, the collar being movable with respect to the housing from a first position to a second position, the second position being closer to the proximal end of the housing than the first position; and a plurality of deformable members, each deformable member extending distally from the collar and being movable through a respective one of the plurality of anchor lumens, the plurality of deformable members being movable with respect to the housing in response to movement of the collar from the first position to the second position, wherein one or more of the plurality of deformable members includes a barb attached to a distal portion thereof, and wherein one or more of the plurality of deformable members includes a suture attached to the barb.

* * * * *